United States Patent [19]

Newkirk

[11] 4,037,604
[45] July 26, 1977

[54] ARTIFICAL BIOLOGICAL DRAINAGE DEVICE

[76] Inventor: John B. Newkirk, P.O. Box 1128, Englewood, Colo. 80110

[21] Appl. No.: 646,574

[22] Filed: Jan. 5, 1976

[51] Int. Cl.² ............................................. A61M 27/00
[52] U.S. Cl. ....................................... 128/350 V; 3/1
[58] Field of Search ............... 128/348, 350 R, 350 V; 3/1

[56] References Cited
U.S. PATENT DOCUMENTS

| 2,969,066 | 1/1961 | Holter et al. | 128/350 V |
| 3,159,161 | 12/1964 | Ness | 128/350 R |
| 3,788,327 | 1/1974 | Donowitz et al. | 128/350 R |

OTHER PUBLICATIONS

Ore et al.-Surgery-Aug. 1962-pp. 385-390, vol. 52, No. 2.

*Primary Examiner*—Dalton L. Truluck
*Attorney, Agent, or Firm*—Richard D. Law

[57] ABSTRACT

A tube for implantation in an animal organ or cavity, for example, an eye, communicates with the anterior chamber of the eye and terminates in a unilateral pressure dependent valve shunt positioned outside the anterior chamber. Lateral side arms secured to the tube provide fixation means to the eye.

10 Claims, 5 Drawing Figures

U.S. Patent   July 26, 1977   Sheet 1 of 2   4,037,604
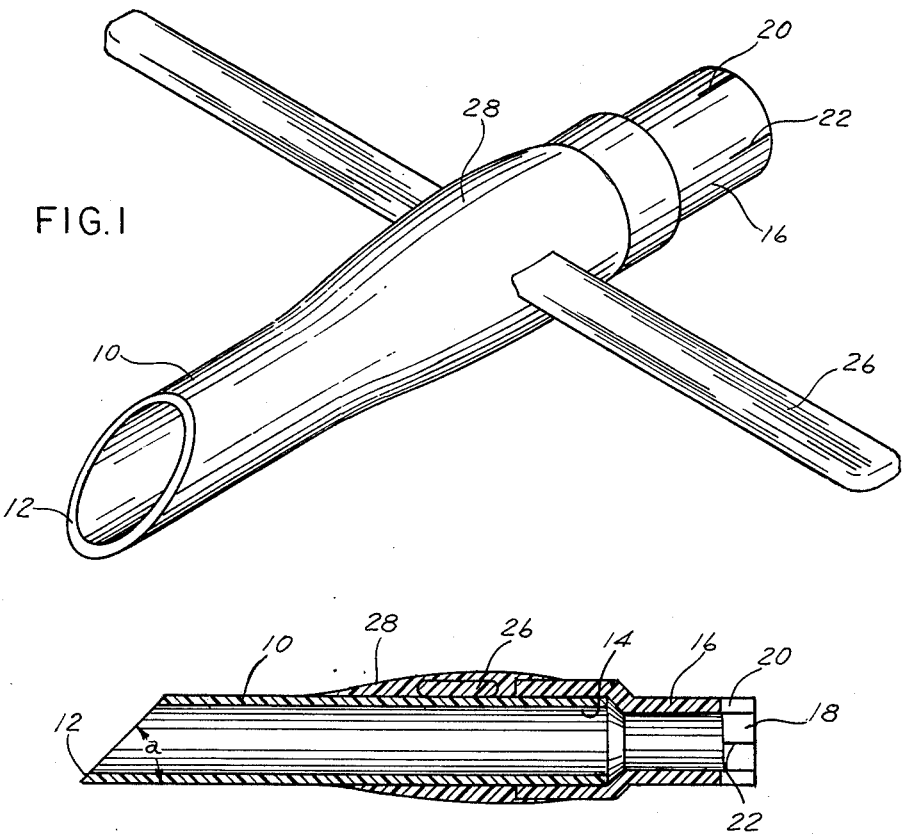
FIG.1
FIG. 2
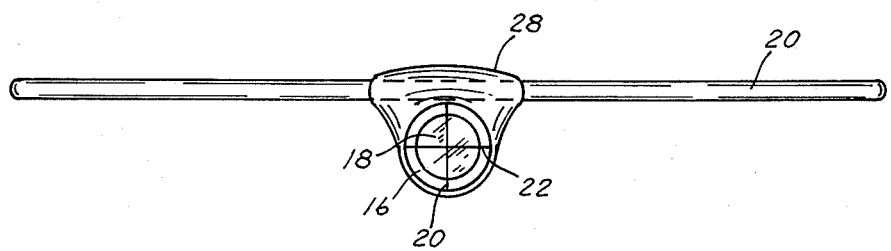
FIG.3

ARTIFICAL BIOLOGICAL DRAINAGE DEVICE

Glaucoma is a disease of the eye characterized by elevated intraocular pressure with subsequent damage to the optic nerve. Experimentally, artificial drainage has been tried over a number of years, but with only short term success. The functioning of these drainage procedures depends upon the created natural opening remaining patent. The intraocular pressure level following these procedures has been found to be variable, with an initial over-function and its associated periods of low intraocular pressure (hypotony). In a number of patients, the surgical opening has, furthermore, scarred closed resulting in failure of the procedure. Such devices as silk thread through the limbus, gel film strips, drain tubes, and the like, have failed for long term control due to the complications of persistent hypotony, fibrosis of the bleb wall, long term development of cataracts, etc. The failure of the glaucoma eye surgery is commonly a result of the scarring over of the sclerostomy site. Other devices have recently been tried to produce a controlled glaucoma regulation. Such devices are, however, bulky and are not suitable for human use.

According to the present invention, there is provided a unidirectionally valved implant for maintaining an opening for the release of aqueous humor from the anterior chamber of the eye, thereby reducing intraocular pressure. The device is a small tube which is surgically implanted into the eye connecting the anterior chamber with the space underneath a scleral flap. The open end of the tube is placed into the anterior chamber, and a blind end containing a pressure dependent unidirectional valve terminates in the space between the sclera and the conjunctive tissues. A lateral wing mounted on the tube is arranged to be secured by a buried suture providing fixation of the device. The device maintains a predictable state of aqueous humor dymanics. Other organs, for example ear drums, may be drained in a similar manner.

A major object of the invention is to provide a microshunt for drainage of small animal organs.

Included among other objects and advantages of the invention is an eye shunt for the control of glaucoma.

Another object of the invention is to provide a tube with one open end and a closed end with a pressure dependent shunt valve for implantation in an eye providing communication between the anterior chamber and the scleral space.

Another object of the invention is to provide a valve shunt for implantation in an eye, which valve consists essentially of a closed end tube with vertical and horizontal closing slits acting as a unidirectional pressure dependent valve.

Another object of the invention is to provide a tubular communication means with a valve shunt for the anterior chamber of an eye and a side arm arranged for fixation purposes as surgical implantation in an eye.

These and other objects and advantages of the invention may be readily ascertained by referring to the following description and appended illustrations in which:

FIG. 1 is an enlarged perspective view of a shunt for optical use according to the invention;

FIG. 2 is a side cross-sectional elevation of the device of FIG. 1;

FIG. 3 is an end-elevational view of the device of FIG. 1;

Figure 4:
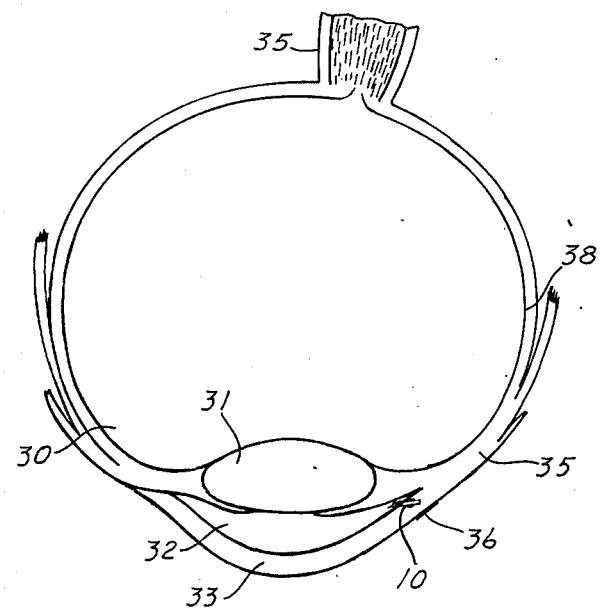
FIG. 4 is a generally schematic cross-sectional view of an eye.

In the device selected for illustration in FIGS. 1–3, the artificial, biological drainage device is of a size and configuration for an eye shunt. The shunt includes a tube 10 having an open end and a diagonally cut open end 12 and a squared open end 14. A soft resilient flexible tube 16 is telescoped over the open end 14 of the tube 10 and terminates a short distance from the end 14 to enclose a portion of the end. The other end of the tube 16 is closed by means of a closure 18. The closure 18 is provided with a vertical slit 20 and a horizontal slit 22, both of which extend only a short distance into the wall of the tube 16, forming the valve for the unit. The flow characteristics of the valve are in part determined and controlled by the lengths of the slits and the material and thickness of the closure 18. A crossarm 26 is secured to the tube 10 by means of a sealant material 28 sealing the crossarm to the tube 10. A single slit may be useful in certain configuration of the drainage device.

The device is arranged for implantation in the eye of a human, and, therefore, must be made of material which is inert and innocuous to all of the tissues and fluids of the eye. The unit, of course, must be made of a size to be accommodated in the eye. In one form, the rigid tubing is 0.38 mm ID and 0.58 mm OD of "Supramid" tubing. This tubing is approximately 2 mm long. The point 12 is formed at about a 45° angle. The soft, flexible tubing is 0.64 mm OD and 0.355 mm ID of medical "Silastic" tubing, extending from 1 to 10 mm or more beyond the end 14 of the rigid tubing. The end of the flexible tubing, of one form, is plugged with Dow-Corning Medical Adhesive A. Furthermore, the entire device, in one form, is coated with the Dow-Corning Medical Adhesive A. The crossarm is formed of about a 6 mm length of the Supramid tubing, formed of about ¼ of the circumference of the wall of a piece of tubing. The crossarm is secured in place by sealing it to the tube 10 by means of Dow-Corning Medical Adhesive A . The slits in the end of the flexible tubing provide a unidirectional valve opening outwardly away from the rigid tubing 10. The valve is a pressure dependent valve and is designed to open from between 12 to 16 mm of mercury, and arranged to close at 2 to 3 mm of mercury less than the opening pressure.

Figure 5:
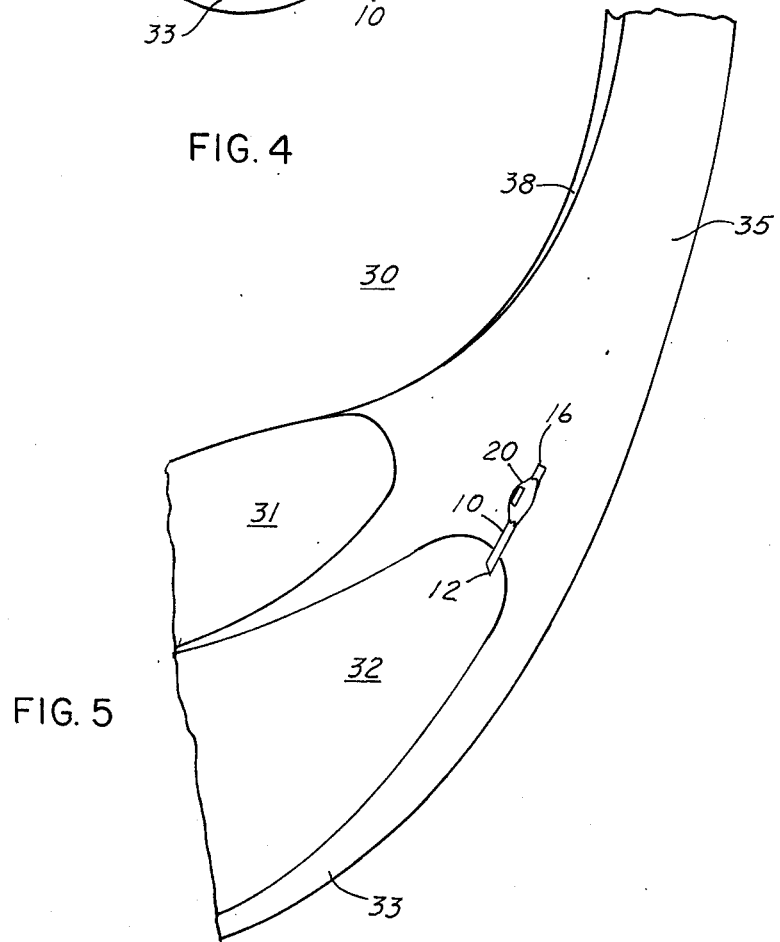
FIG. 5 is a highly enlarged, cross-sectional detail of an eye with a shunt implanted into the eye, according to the invention.

As illustrated in FIGS. 4 and 5, the valve shunt is implanted in the eye with the open end of the rigid tube usually in the angle of the anterior chamber of the eye and with the valve end in the sclera of the eye. The general cross-cross section of the eye, illustrated in FIG. 4, shows a major part of the eye with a posterior chamber 30 having a lens 31 in the front part of the chamber and the optic nerve 32 extending outwardly from the rear of the chamber. The anterior chamber 32 is positioned in front of the lens and is covered by the cornea 33. The cornea is extended into the sclera 35 at the conjunctiva 36 which extends around the cornea. The sclera covers the choroid of the eye which extends around the posterior chamber. The anterior chamber of the eye is filled with an aqueous humor. In the disease glaucoma the pressure of the aqueous humor increases so that there is an increased tension within the eye. The valve shunt of the present invention is implanted through incision, for example, under the lamellar scleral flap, as shown in FIG. 5, where the open end 12 of the tube 10 is placed in the anterior chamber in open communication with the aqueous humor. The lateral arms are secured in place by a suture. The flexible tube 16 with the valve remains outside the eye under the scleral flap. The implant functions as a communication between the anterior chamber and the intrascleral-subconjunctival space. When the pressure in the anterior chamber increases above the designed opening pressure of the valve, between 12-16 mm Hg, for example, aqueous humor flows out of the anterior chamber through the valve, thus lowering interaocular pressure. The valve closes at from 2 to 3 mm less than the opening so as to reduce hypotony, and its complications are thereby avoided.

The valve of the eye shunt may be made to open at a predetermined pressure range by the length of the slits into the tubing wall, thickness of the tube closure, etc. The closing of the tube should be a slight pressure below the opening pressure so as to maintain a pressure in the anterior chamber and prevent hypotony. For example, a valve arranged to open at 15 mm Hg closes at 13 mm Hg; a valve opening at 24 mm Hg closes at 22 mm Hg; a valve opening at 11 mm Hg closes at 10 mm Hg, etc. Thus, when a valve opens in the range of 10-25 mm Hg, it closes at 1-3 mm Hg below the opening pressure. A valve may, therefore, be chosen to provide the pressure prescribed by the physician. The valve must be capable of passing the flow necessary to maintain the described pressure.

Since the shunt is a long term implant, it must be innocuous to the tissues and fluids with which it is in contact. It cannot be absorbed, corroded, etc. during its long period of contact. A number of materials are available to meet the engineering and medical specifications of the shunts.

The device has been illustrated with crossed slits at the outer end of the shunt; however, it may be made with a single slit, either horizontal or vertical, in relation to the crossarm. The single slit may be made of a length to produce the desired pressure for opening, depending on wall thickness, tube closure thickness, tube and tube closure durometer, etc. The length of the device is generally determined by the desired positioning of the valve end, as to where to discharge the fluid exiting the valve. This may be determined by the doctors for the patient.

What is claimed is:

1. An artificial biological drainage device such as an eye shunt, comprising:
    a. a plastic, body innocuous tubular body being sufficiently rigid to maintain its shape on being implanted in a human body and having two open ends;
    b. a soft, flexible tube contacting and peripherally secured to and telescoped over one end of said tubular body and having a soft, resilient closure forming a closed end for said tubular body, there being at least one slit in said closed end arranged to open outwardly providing a unidirectional valve for fluid above a predetermined pressure and arranged to close at a pressure slightly less than the opening pressure for maintaining fluid pressure in an eye at a generally predetermined level; and
    c. a crossarm secured to said tubular body for securing the same in an implanted position all said parts being innocuous to the tissues and fluids in a body and being of a size to be accommodated in implant in a small organ.

2. A drainage device according to claim 1 wherein said tubular body has a free, pointed end and a square end telescoped in said flexible tube.

3. A drainage device according to claim 1 wherein said tubular body is an essentially rigid plastic.

4. A drainage device according to claim 1 wherein said device is covered by an innocuous, human body compatible covering.

5. A drainage device according to claim 1 adapted as an eye shunt wherein said tubular body is 1-3 mm long and said flexible tube is at least about 1-10 mm long.

6. A drainage device according to claim 5 wherein said tubular body is a nominal 2 mm tube with an opening therethrough.

7. A drainage device according to claim 5 wherein said crossarm is about 6 mm long.

8. A drainage device according to claim 1 wherein said at least one slit is crossed slits which extend only a short distance into the wall of said flexible tube.

9. A drainage device according to claim 1 wherein said closure is cylindrical and of a full diameter of the internal diameter of said flexible tube.

10. A drainage device according to claim 1 adapted as an eye shunt wherein said valve is arranged to open at a pressure of 10-25 mm Hg and to close at from 1-3 mm Hg less than the pressure necessary to open it.

* * * * *